United States Patent [19]

Couch

[11] Patent Number: 4,584,531
[45] Date of Patent: Apr. 22, 1986

[54] NONCONTACT ELECTROSTATIC HOOP PROBE FOR COMBUSTION ENGINES

[75] Inventor: Robert P. Couch, Palm Beach Gardens, Fla.

[73] Assignee: United Technologies Corporation, Hartford, Conn.

[21] Appl. No.: 432,507

[22] Filed: Oct. 4, 1982

[51] Int. Cl.[4] .................. G01R 5/28; G01R 29/12
[52] U.S. Cl. .................................................. 324/464
[58] Field of Search .............. 324/72.5, 109, 149, 324/158 P, 452, 457, 459, 464, 465, 468; 343/753, 705, 741, 708; 73/116; 340/683

[56] References Cited

U.S. PATENT DOCUMENTS

| | | | |
|---|---|---|---|
| 3,114,877 | 12/1963 | Dunham | 324/464 |
| 3,449,667 | 6/1969 | Gourdine | 324/464 |
| 3,541,431 | 11/1970 | Maise et al. | 324/464 |
| 3,544,888 | 12/1970 | Sellen, Jr. | 324/457 |
| 3,589,869 | 6/1971 | Scolnick | 324/464 |
| 3,679,973 | 7/1972 | Smith, Jr. et al. | 324/464 |
| 3,775,763 | 11/1973 | Couch et al. | 340/683 |
| 4,321,546 | 3/1982 | Schneider, Jr. | 324/457 |
| 4,456,883 | 6/1984 | Bullis et al. | 324/459 |

OTHER PUBLICATIONS

R. P. Couch, "Detecting Abnormal Turbine Engine Deterioration Using Electrostatic Methods" in *Journal of Aircraft*, vol. 15, Oct. 1978, pp. 692–695.

F. L. Baker, "Electronic Analysis of Electrostatic Pulses to Detect Imminent Jet Engine Gas-Path Failure", Air Force Institute of Technology Thesis AFIT/GE/EE/77-7, Dec. 1977.

Sajben, M. et al., "Evaluation of Experiments Using Electrostatic Probes . . . ", Air Force Flight Dynamics Laboratory, Wright Patterson AFB, AFFDL-TR-7-5-74, Jul. 1975.

Dunn, R., "The Electrostatic Sensing of Simulated MA-1A Gas-Path Distress", Air Force Institute of Technology, Wright Patterson AFB, Thesis GNE/PH/75-4, Dec. 1975.

Primary Examiner—Stewart J. Levy
Assistant Examiner—Stephen M. Baker
Attorney, Agent, or Firm—M. P. Williams; Gerald E. Linden

[57] ABSTRACT

A short-circuited loop of conductor 10, 32, 44, 54 comprises an electromagnetic short-circuit hoop probe which is electrically insulated from a gas stream passing therethrough either by spatial isolation (FIG. 2) or by a coating of electrical insulation (FIGS. 3-5), whereby to reduce noise and DC current levels which could otherwise pollute signals of interest therein. A large hoop version of the non-contact probe permits electrostatic diagnostics of gas streams downstream of flame (FIG. 2).

5 Claims, 6 Drawing Figures

NONCONTACT ELECTROSTATIC HOOP PROBE FOR COMBUSTION ENGINES

TECHNICAL FIELD

This invention relates to electrostatic monitoring of combustion engines, and more particularly to short-circuited and noncontacted electrostatic hoop probes therefor.

BACKGROUND ART

In the past decade, monitoring of the electrical characteristics of gas flowing through a jet engine has been studied as a possible indication of engine deterioration. Apparatus disclosed in U.S. Pat. No. 3,775,763 utilizes an electrostatic probe positioned in the exhaust of the jet engine, such as through the tail pipe wall. Abnormal conditions were thought to be coupled with small particles striking the probe and causing spikes of ion current of a relatively large magnitude. Subsequently, it was theorized that the signals did not result from individual particles of metal hitting the probe, but rather that the signals were indicative of Trichel pulses (a form of repetitive corona discharge) created by high potential pockets of excess charge. This is as reported by Couch, R.P.: "Detecting Abnormal Turbine Engine Deterioration Using Electrostatic Methods", *Journal of Aircraft*, Vol. 15, October 1978, pp 692-695. A probe set including circular insulated segments within the gas turbine engine tail pipe and a triangle of wire extending through the tail pipe exhaust gas path were developed. With these probes, a normalized count of probe current (or voltage developed across an impedance) in excess of a threshold magnitude over a period of time definitely correlated with impending engine component malfunctions or severe deterioration. As reported in the aforementioned article, however, the use of normalized counts of large magnitude signals from the ring and grid probe was thought to provide reliable prediction of only two out of three gas-path failures, at best, without any distinction between possible causes thereof.

The limited results achievable with the grid and ring probe counting method described in the aforementioned article is due in part to the fact that the very high noise levels on the probes preclude use of a sufficiently low threshold to be sensitive to ionic phenomenon of lower magnitude. Additionally, the excessive noise masks the characteristics of ion phenomena, other than the occurrence of extremely large signals. In order to improve the reliability of prediction of an impending failure, and to discriminate, with a useful degree of success, between types of impending failure, much improvement in signal-to-noise ratio of the sensing probes is required.

Additional details of the segmented ring reported in the article can be found in Appendix C of Baker, F. L., "Electronic Analysis of Electrostatic Pulses to Detect Imminent Jet Engine Gas-Path Failure", Air Force Institute of Technology Thesis AFIT/GE/EE/77-7, December 1977 (Defense Documentation Center No. AD-AO56515). On the one hand, it is believed that the prior tail pipe semi-continuous ring has a poor signal response because it is disposed adjacent a large ground plane, namely, the tail pipe of the engine. Additionally, the semi-continuous ring has connecting segments outside of the ground plane that are responsive to both electrostatic and electromagnetic influences not within the gas path of the engine. It can therefore be understood that the signal-to-noise ratio of such a probe must inherently be poor.

Both the semi-continuous ring and the triangular grid probe are additionally noisy because of the large areas thereof that are subjected to material flowing through the gas path; in other words, a significant portion of material flowing through the gas path can contact these probes. This is particularly true of the triangular grid probe. The direct contact of these probes by particles in the gas path, in addition to electrostatic charge induced thereon, renders these probes inherently noisy with poor signal-to-noise differentiation, and they develop net current flow due to charges impinging thereon.

A recent innovation in the control of internal combustion engines, is described in a commonly owned copending U.S. patent application entitled "Method and Apparatus for Indicating an Operating Characteristic of an Internal Combustion Engine" filed contemporaneously herewith by Bullis et al, Ser. No. 432,501. Therein, the electrostatic charge of pulses of reciprocating, internal combustion engine exhaust provide an indication of solid carbon content, and therefore of the relative completeness of combustion in, and timing of, the engine. However, it has been found that use of a common, conductive shaft as a probe results in a very high DC current level and noise which tend to mask the pulses which are desired to be detected.

In high performance military gas turbine engines, the inclusion of an afterburner would render the aforementioned grid and ring probes useless, since they would be totally burned away. Additionally, probes disposed at the end of a gas turbine engine core are incapable of monitoring events within the afterburner itself. Thus, probes known to prior art are not useful for monitoring performance of the afterburner in military engines.

In many instances, it is desirable to employ electrostatic diagnostics with respect to a combustion engine without first having to modify the engine (such as the installation of the grid or rings as described in the aforementioned article).

DISCLOSURE OF INVENTION

Objects of the invention include provision of an electrostatic probe which may be used in conjunction with a gas turbine engine without engine modification, which has higher signal sensitivity, which is less sensitive to current phenomena and productive of unwanted noise, less and which may be used in a wide variety of combustion engine monitoring circumstances, configurations and signal processing methodology.

According to the present invention, an electrostatic hoop probe for use with combustion engines comprises an electromagnetic short-circuit which is isolated or insulated from contact by electrostatic charge. According further to the invention, an electrostatic probe for use with a gas turbine engine comprises a short-circuit hoop having a diameter in excess of the diameter of any exhaust plume, the electrostatic activity of which is to be monitored thereby. In still further accord with the invention, an electrostatic hoop probe is disposed at a distance from the common potential ground of the engine being monitored thereby. In further accord with the invention, an insulated hoop provides the characteristics of a noncontacting hoop.

The invention is readily implemented in a variety of ways using apparatus and techniques which are readily available in the art, in the light of the detailed teachings with respect thereto which follow hereinafter. The invention is easily used with a wide variety of electronic signal processing equipment.

The invention, by sensing electrostatic charge and being insensitive to electromagnetic fields, provides a higher electrostatic signal-to-noise ratio. In fact, a six-foot diameter hoop probe of the invention has less noise than a one inch long insulated conductive shaft probe. The invention, being a noncontacting probe, provides the opportunity for monitoring electrostatic charge in a gas plume passing therethrough, without interference due to collisions of particles or charges directly on the probe, and without destruction by flame. When configured in a flow contact environment, such as along the exhaust pipe of a reciprocating engine, or adjacent the inner wall of a gas turbine engine tail pipe, an electrically insulating coating or cover prevents direct charge impingement to avoid D.C. levels, noise and charge leak-off current effects attendant probes known in the art. Such a coating also provides a hermetic seal to avoid unwanted shorting. This aspect of the invention may be implemented by a conductor imbedded in a gasket (such as in a tail pipe flange).

Other objects, features and advantages of the present invention will become more apparent in the light of the following detailed description of exemplary embodiments thereof, as illustrated in the accompanying drawings.

BEST MODE FOR CARRYING OUT THE INVENTION

Figure 1:
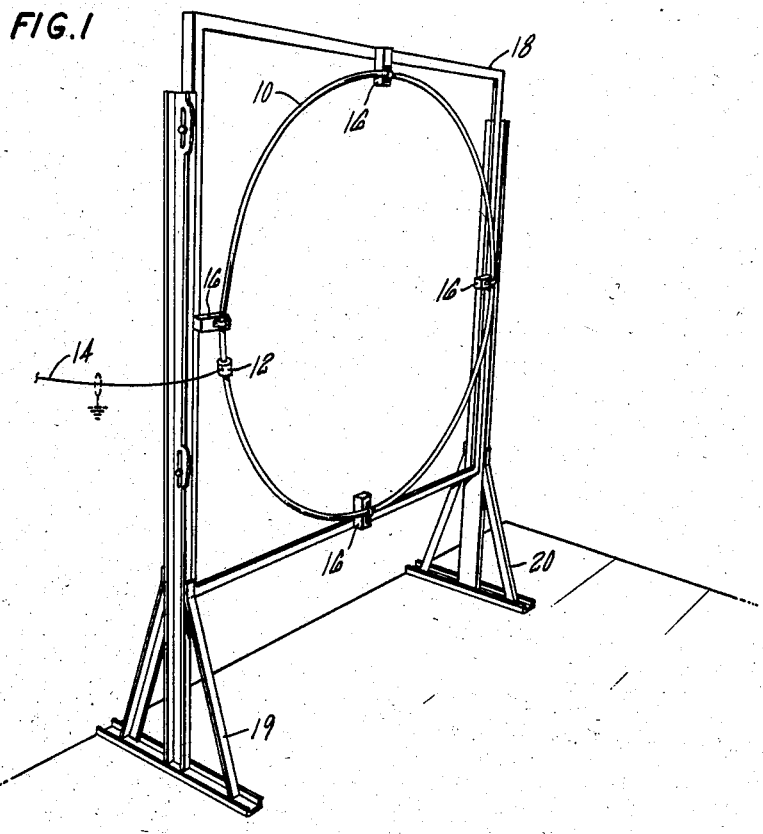
FIG. 1 is a perspective view of a short-circuit, noncontact, electrostatic probe in accordance with the present invention.

Referring now to FIG. 1, a noncontacting electrostatic probe of the present invention comprises an electrical conductor 10 closed on itself so as to provide a completely short-circuited hoop, the conductor 10 is electrically connected, such as by a clamp 12 to a conductor 14, such as shielded coaxial cable. The conductive hoop 10 is suspended on insulating struts 16 which are supported by a suitable frame 18. The frame 18 may be bolted to stands 19, 20, either through slots or not, depending upon whether adjustment of the height of the hoop 10 is desired or not.

Figure 2:
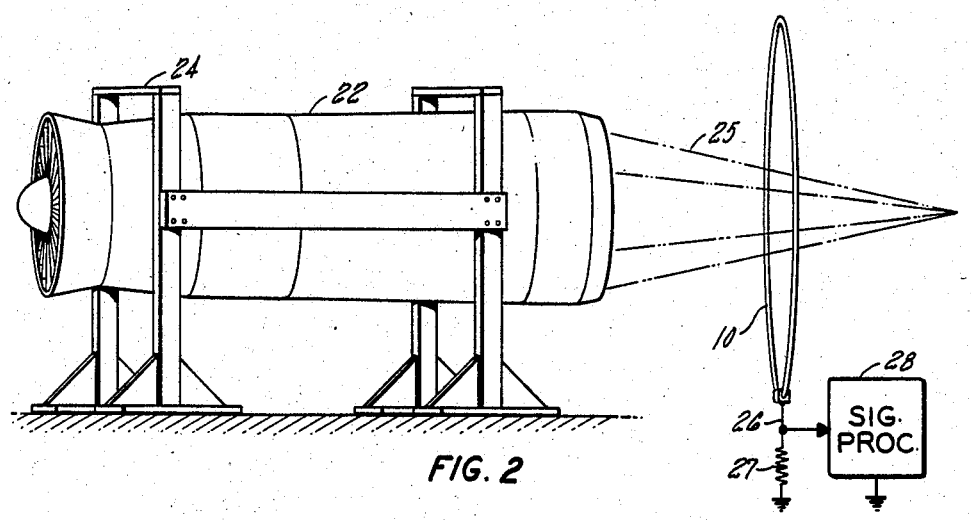
FIG. 2 is a simplified, schematic perspective view illustrating the monitoring of the exhaust plume of a gas turbine engine in accordance with the invention.

In FIG. 2, a gas turbine engine 22 is shown disposed on a test stand 24 with the hoop 10 schematically illustrated as being disposed aft of the engine with the exhaust plume 25 of the engine flowing through the hoop 10, but not contacting it. Typically, the exhaust plume may be on the order of three feet in diameter for a very large engine and as small as one-half foot for a smaller gas engine, whereas the hoop of the embodiment shown in FIGS. 1 and 2 may be on the order of 4 to 6 feet in diameter, as appropriate. However, even the smallest of engines can be electrostatically diagnosed using a shorted hoop of the invention which is on the order of 6 feet in diameter, the relationship between the size of the plume 25 and of the hoop 10 only being that the hoop 10 should be large enough so that the plume does not contact it when such is the desired case. For instance, if the engine 22 is an afterburning engine, the plume 25 may actually be flame, when the afterburner is lit. On the other hand, if a wholly noncontact electrostatic test is desired in the absence of flame, the hoop 10 may also be larger than the plume so as to reduce the noise and charge leak-off effects which result from charges and particles contacting the probe. The hoop 10 is shown connected by a lead 26 through a resistor 27 to ground. The resistor 27 is preferably of a moderate size, such as on the order of 50K–100K Ohms, to provide a voltage indicative of the time rate of change of charge passing through the hoop which is useful for handling in a signal processor 28 (on the order of a volt). The signal processor 28 may take a variety of forms, including that described in the aforementioned article. However, the true value of the embodiment of the invention shown in FIGS. 1 and 2 is achieved only by using more sophisticated signal processing.

Figure 3:
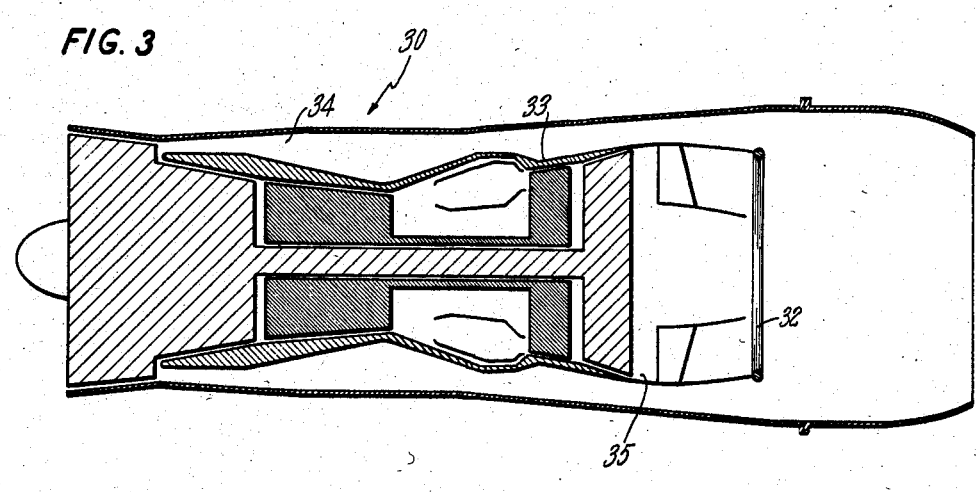
FIG. 3 is a simplified, sectioned side elevation of a turbofan engine employing an embodiment of the invention at the wake of the fan/core splitter walls.

Referring now to FIG. 3, a non-afterburning turbofan engine 30 has a noncontact E/M shorted hoop 32 of the present invention disposed adjacent to and downstream of the fan/core splitter 33 that separates the fan duct 34 from the core exhaust 35. The hoop 32 is disposed on the splitter by means of insulators, and the electrical lead thereto (not shown) is brought out such as by means of coaxial cable through or adjacent to supporting struts (in the same fashion that pressure and temperature detectors are connected in an engine). This utilization of a shorted hoop in accordance with the invention is advantageous since the hoop 32 is disposed in an aerodynamic neutral zone (specifically, the wake of the fan/core splitter); thus it should not affect engine operation. The characteristics of a noncontacting probe (such as shown in FIGS. 1 and 2) are achieved by suitably insulating the entire probe 32, such as with a coating of Teflon, in addition to being insulated from the metallic parts of the engine. The hoop 32 may be a solid ring of metal or it may be fiberglass or suitable organic material or composite with a metallic coating, film or cladding thereon.

Figure 4:
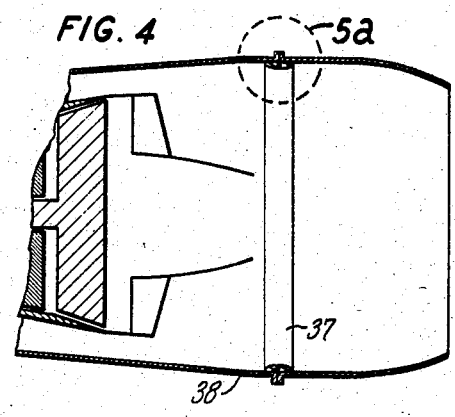
FIG. 4 is a partial, simplified, sectioned side elevation view of the tail pipe of a turbofan engine illustrating an embodiment of the invention disposed around and adjacent to the tail pipe of the engine.
Figure 5:
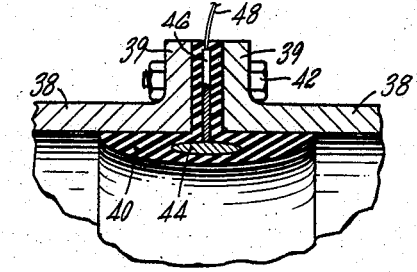
FIG. 5 is a partial, sectioned side elevation view of an embodiment of the invention imbedded in the flange gasket of a turbofan engine, as at the dotted circle 5a in FIG. 4.

In FIG. 4, a hoop 37 in accordance with the invention is shown disposed adjacent the tail pipe wall of a turbofan engine (of the same type illustrated in FIG. 3). This may comprise a hoop of insulating material (such as fiberglass or the like) with a suitable metallic layer on the internal surface thereof, disposed directly to the tail pipe wall, the metallic layer also being insulated from the charges in the gas. Or, it may take the form illustrated in FIG. 5. In FIG. 5, the tail pipe wall 38 is illustrated as having flanges 39 which are separated by an insulating gasket 40 which may be neoprene or the like, the tail pipe being assembled by sandwiching the gasket 40 between the flanges such as by means of bolts 42. Disposed within the insulating gasket 40 is a metallic ring 44 which comprises a shorted hoop in accordance with the present invention, having a conductor 46 leading through the gasket material (at other than a station of one of the bolts 42) to an electrical lead 48 (equivalent to the lead 26 in FIG. 2). This provides an engine-mounted hoop which is hermetically sealed and which is insulated from the gas passing adjacent thereto so that it has the characteristics of a noncontacting hoop.

Figure 6:
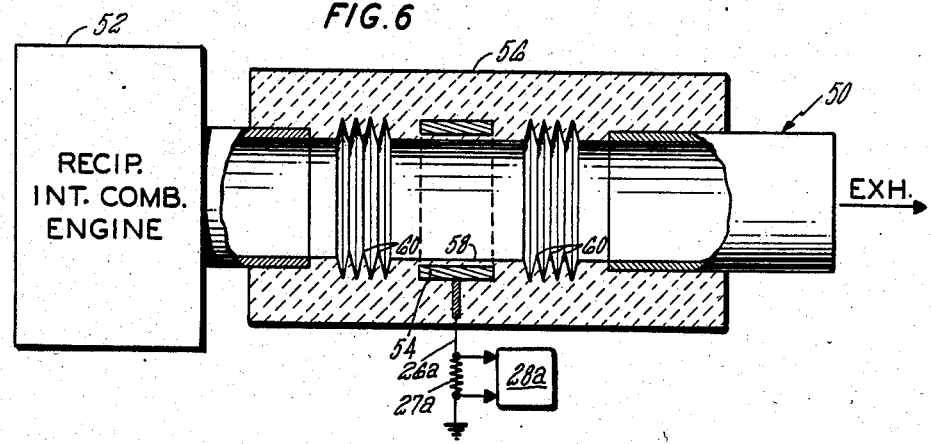
FIG. 6 is a simplified, sectioned side elevation view of an embodiment of the invention useful in the exhaust pipe of an internal combustion reciprocating engine.

Referring now to FIG. 6, the exhaust pipe 50 of a reciprocating internal combustion engine 52 is provided with a non-shorting, noncontact, E/M short circuit hoop probe in accordance with the present invention. A hoop 54 of conducting material is imbedded in a block 56 of insulating material, the insulating material 56 being fitted to the exhaust pipe 50 in an obvious fashion. The hoop 54 is rendered noncontacting by being embedded in the insulating material 56, even at the internal, gas path wall 58 thereof. In order to avoid short circuiting of the insulating material 56, sharp protrusions 60 may be provided in the material on either side of the hoop. Thus, the flow of gas in the tail pipe 50 would tend to keep at least the inner sharp edges relatively clean so as to not short circuit the hoop 54 to the ground plane which comprises the exhaust pipe 50 or other engine parts. If soot builds up in the region 58, it is irrelevant since a hoop in accordance with the present invention can sense the passage of excess charge therethrough even though there is a hydrocarbon conductivity plane between it and the gas path within which the charge is flowing. This is another feature of the present invention: the presence of an ungrounded conductive layer between the hoop of the invention and the charge which it is sensing does not render the hoop insensitive to such charge.

The hoop 54 is connected through the insulator 56 to a suitable lead 26a and through a signal-developing resistor 27a so as to provide a voltage indicative of time rate of change of charge in signal processing apparatus 28a. In the case of an internal combustion engine, the signal processing apparatus 28a may differ considerably from the signal processing apparatus 28 of FIG. 2. Where found to be desirable, the embodiment of FIG. 6 may be used with apparatus disclosed in the aforementioned Bullis et al application.

The axial extent of a hoop probe in accordance with the invention may vary considerably, depending upon the application thereof. Thus, small diameter wires, larger diameter pipes, or cylinders ranging in length from fractions of an inch to several inches or more may be utilized. The use of long cylinders is permissible because the nature of the charge passing through an electromagnetic noncontacting short circuit can be shown to conform to Gauss' law. Thus a signal indication of the entrance and exit of the charge from the hoop will be present. However, for processing signals having a particular waveform significance as in the aforementioned Bullis et al application, short hoops are to be preferred.

The test stand hoop of FIGS. 1 and 2 is obviously useful for testing engines which either do not have engine-mounted probes therein or in cases where absolute noncontact electrostatic probe characteristics are desirable. On the other hand, the engine-mounted hoops described with respect to FIGS. 3-5 are useful for in-flight monitoring of engine electrostatic charges, when off-engine probes are impractical.

Of course, any probe which is actually immersed in flame must be able to withstand it; therefore, the noncontact characteristic of the embodiment of FIGS. 1 and 2 has the aforementioned additional advantage of being immune to the flame which it surrounds (when flame is present), since it is not contacted thereby.

As described briefly hereinbefore, the electromagnetic short-circuited hoops of the present invention may be comprised, depending upon the application and utilization intended therefor, of solid metal hoops, fiberglass, phenolic or composite material hoops with suitable cladding films or strands of conductors disposed appropriately thereon. As described briefly hereinbefore, a hoop in accordance with the invention will work more effectively if it is not very close to an adjacent ground plane (such as that illustrated in FIGS. 4 and 5) but being an electromagnetic short circuit, it serves better adjacent a ground plane than does the segmented ring of the prior art described hereinbefore. Insulation of probes which otherwise are not wholly noncontacting (such as those described in FIGS. 3-5) may be accomplished by suitable electrically insulative coatings depending upon the particular environment in which they are to be utilized, in accordance with skill of the art. The shape and dimensions of the probes (although described as hoops herein) also may depend upon the environment in which they are to be used. For instance, the hoop lends itself to engines and tail pipes of circular cross section. However, the invention may be practiced with loops of other shapes, including triangles, when the loop is rendered noncontacting (insulated) either by having a suitable dimension (an internal least dimension, such as the diameter of a circle or the distance from the centroid of a rectangle to the nearest portion of the loop) to take it beyond the possibility of electrically conducting contact with the gas stream or by insulating it with a suitable covering. An advantage of the invention is that since it is an encompassing, electromagnetic short circuit, the pattern of electrostatic charge passing therethrough can (as shown in the embodiments herein) include all of the charge in the included gas path (in contrast with the grid of the prior art or rod-like probes which are not necessarily responsive to all of the charge). Furthermore, because the nature of the charge passing through an electromagnetic noncontacting short circuit conforms to Gauss' law, the exact size of the hoop is generally not critical (subject to field strength alone), as described briefly hereinbefore. The isolated hoop of FIGS. 1 and 2 will have high signal strength (compared to the grid and ring of prior art) since it is not near a ground plane.

Thus, although the invention has been shown and described with respect to exemplary embodiments thereof, it should be understood by those skilled in the art that the foregoing and various other changes, omissions and additions may be made therein and thereto, without departing from the spirit and the scope of the invention.

I claim:

1. A noncontact electrostatic hoop probe adapted to sense the passage of electrostatic charge in a stream of exhaust gas effluent from an internal combustion engine, comprising a loop of electrical conductor closed upon itself to provide an electromagnetic short circuit, said loop having an internal least dimension sufficiently large to ensure spatial separation of said probe from substantially all components of a gas stream passing therethrough when in use so that there is no physical contact between the effluent and the loop.

2. A noncontact electrostatic hoop probe adapted to sense the passage of electrostatic charge in a stream of exhaust gas effluent from an internal combustion engine, comprising a loop of electrical conductor closed upon itself to provide an electromagnetic short circuit, said loop being completely covered with an electrical insulation material, whereby said probe is isolated from electrical contact by all components of any gas stream passing therethrough or thereby.

3. The method of sensing electrostatic net charge in a gas stream which comprises surrounding a short section of the gas stream with an electromagnetic short circuit which is electrically insulated from said gas stream.

4. The method of claim 3 wherein said gas stream is surrounded by an electrically conductive loop, short circuited on itself, having a least dimension sufficiently greater than the cross section of said gas stream thereat, and positioned with respect thereto, to spatially isolate said loop from said gas stream.

5. The method of claim 3 wherein said gas stream is surrounded by a loop covered with electrical insulation.

* * * * *